United States Patent [19]

Haugwitz et al.

[11] 4,181,663
[45] Jan. 1, 1980

[54] SELENIUM CONTAINING DERIVATIVES OF PROLINE AND PIPECOLIC ACID

[75] Inventors: Rudiger D. Haugwitz; Frank L. Weisenborn, both of Titusville, N.J.

[73] Assignee: E. R. Squibb & Sons, Inc., Princeton, N.J.

[21] Appl. No.: 7,070

[22] Filed: Jan. 29, 1979

[51] Int. Cl.$^2$ .................. C07D 403/12; C07D 207/16
[52] U.S. Cl. ............................ 260/326.25; 260/326.2; 260/326.46; 260/326.47; 424/207; 424/274; 546/189; 546/245
[58] Field of Search ...................... 260/326.25, 326.46, 260/326.47; 546/189, 245

[56] References Cited

U.S. PATENT DOCUMENTS

| | | | |
|---|---|---|---|
| 4,046,889 | 9/1977 | Ondetti et al. | 260/326.47 |
| 4,091,024 | 5/1978 | Ondetti | 260/326.25 |
| 4,105,776 | 8/1978 | Ondetti et al. | 260/326.47 |
| 4,129,571 | 12/1978 | Ondetti et al. | 260/326.47 |

*Primary Examiner*—Mary C. Lee
*Attorney, Agent, or Firm*—Lawrence S. Levinson; Stephen B. Davis

[57] ABSTRACT

New selenium containing derivatives of proline and pipecolic acid which have the general formula

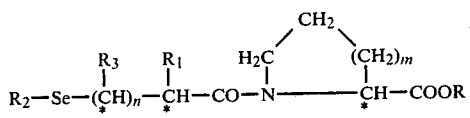

are useful as hypotensive agents.

13 Claims, No Drawings

SELENIUM CONTAINING DERIVATIVES OF PROLINE AND PIPECOLIC ACID

SUMMARY OF THE INVENTION

This invention relates to new selenium containing derivatives of proline and pipecolic acid which have the general formula

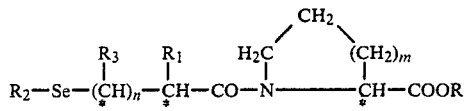

wherein
R is hydrogen, lower alkyl, phenyl or phenyl-lower alkyl;
$R_1$ and $R_3$ each is hydrogen or lower alkyl;
$R_2$ is hydrogen, lower alkyl, lower alkanoyl, benzoyl, phenyl, phenyl-lower alkyl or

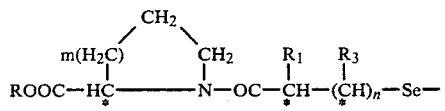

m is 1 or 2; and
n is 0, 1 or 2.

The asterisks indicate asymmetric carbon atoms. The carbons in the acyclic side chain is asymmetric when it bears a lower alkyl substituent.

BACKGROUND OF THE INVENTION AND PRIOR ART

In U.S. Pat. Nos. 4,046,889 and 4,105,776, Ondetti and Cushman disclose that thioalkanoyl derivatives of azetidinecarboxylic acid, proline and pipecolic acid having the general formula

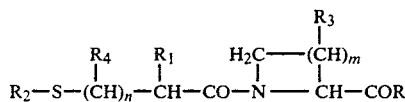

are useful as angiotensin converting enzyme inhibitors which reduce blood pressure. We have now found that selenium derivatives of formula I above also have blood pressure reducing properties.

DETAILED DESCRIPTION OF THE INVENTION

The invention in its broadest aspects includes proline and pipecolic acid derivatives having formula I above. Within this group are preferred those compounds of formula I wherein R is hydrogen or lower alkyl, especially ethyl; $R_1$ is hydrogen or lower alkyl, especially methyl; $R_2$ is hydrogen, lower alkanoyl, especially acetyl, phenyl, phenylmethyl or the bis forming radical; $R_3$ is hydrogen; m and n each is 1 or 2, especially 1.

The stereoisomers in which the amino acid moiety is proline and is in the L-form are especially preferred.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The $C_1-C_4$ members, especially $C_1$ and $C_2$ members, are preferred. The phenyl-lower alkyl groups include lower alkyl groups of this same kind and the same preferences apply. Phenylmethyl is especially preferred.

The lower alkanoyl groups are those having the acyl radicals of the lower ($C_2-C_7$) fatty acids, for example, acetyl, propionyl, butyryl, isobutyryl and the like. The lower alkanoyl groups having up to four carbons, and especially acetyl, are preferred.

When $R_2$ is the radical

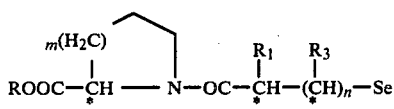

which forms a bis compound or "dimer", the symmetrical bis compound is preferred and the same preferences described above for the substituents represented by the variables apply to such compounds.

The products of formula I can be produced by various methods of synthesis. According to one preferred method, an acid or ester having the formula

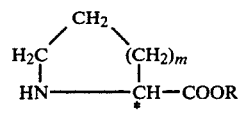

wherein R is hydrogen or lower alkyl, e.g., proline, pipecolic acid or lower alkyl esters thereof, is coupled with a haloalkanoic acid having the formula

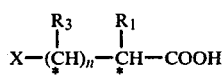

wherein X is a halogen, preferably chlorine or bromine, by one of the known procedures in which the acid II is activated, prior to reaction with the acid of formula III, involving formation of a mixed anhydride, symmetrical anhydride, acid chloride, active ester or the like. In this connection, see Houben-Weyl, *Methoden der Organischen Chemie.*, Synthese von Peptiden Teil II, Vol. XV/2, 1–364 (Thieme Verlag, Stuttgart, 1974).

The product of this reaction is a compound having the formula

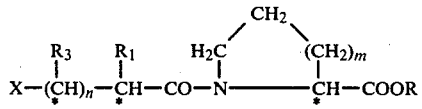

This product is then made to react with a selenol having the formula $$R_5SeH \qquad (V)$$

wherein $R_5$ is lower alkyl, phenyl or phenyl-lower alkyl,
e.g., in an inert organic solvent like methanol, ethanol, acetonitrile, ethyl ether or the like.

The selenol of formula V can be conveniently prepared by reducing a diselenide $(R_5Se)_2$ with sodium borohydride, lithium aluminum hydride or the like in a solvent such as ethyl ether or tetrahydrofuran.

Another preferred method for synthesizing products of formula I wherein n is 1 comprises reacting the selenol of formula V with a starting material which has the formula

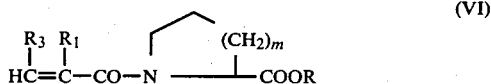

e.g., in an inert organic solvent like methanol, ethanol, acetonitrile or ethyl ether.

The bis compounds, i.e., compounds of formula I wherein $R_2$ is the selenoacylprolyl or selenoacylpipecolic acid radical are produced by reacting a compound of formula IV with an alkali metal selenide like disodium diselenide ($Na_2Se_2$). The disodium diselenide is prepared by reacting selenium and sodium borohydride in water or ethanol [See J.A.C.S. 95, 197(1973)].

Alternatively, these bis compounds can be prepared by reacting a diselenodialiphatic acid having the formula

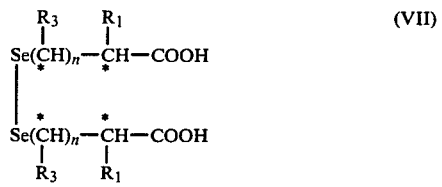

with an acid or ester of formula II utilizing a mixed anhydride, acid chloride or the like, as described above.

The dimer can also be converted to the corresponding monomer wherein $R_2$ is hydrogen, by reduction, e.g., with sodium borohydride.

Compounds of formula I wherein $R_2$ is lower alkanoyl or benzoyl can also be produced from a compound of the formula

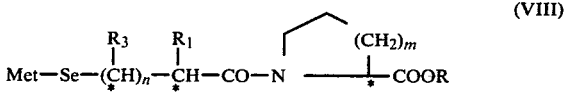

(derived by the reduction of the bis compound as described above). "Met" represents a metal like sodium, magnesium or lead. The compound of formula VIII is reacted with a lower alkanoyl halide or benzoyl halide $R_6$—CO—hal wherein $R_6$ is lower alkyl or phenyl, in a reaction medium like pyridine. For additional details see *Organic Selenium Compounds: Their Chemistry and Biology*, Ed. by Klayman and Gunther (John Wiley & Sons, New York, 1973) pages 263-271.

Reactions involving selenium or selenium-containing compounds are best run under an inert atmosphere, e.g., nitrogen, to prevent oxidation.

Products of formula I having one asymmetric carbon and two or more if $R_1$ and/or $R_3$ are other than hydrogen. These carbon atoms are indicated by asterisks in formula I. The compounds accordingly exist in stereoisomeric forms or in racemic mixtures thereof. All of these are within the scope of the invention. The above described synthesis can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitute the preferred isomeric form.

The compounds of this invention form salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product, in the same manner as illustrated in the examples for isolating intermediates as dicyclohexylamine salts.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II by angiotensin converting enzyme and therefore are useful in reducing or relieving angiotensin related hypertension, for example renovascular hypertension or malignant hypertension. By the administration of a composition containing one or a combination of compounds of formula I or physiologically acceptable salt thereof, angiotensin dependent hypertension in the species of mammal suffering therefrom, e.g., rats, cats, dogs, etc., is alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance is these compositions or preparations is such that a suitable dosage in the range indicated is obtained.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention and constitute especially preferred embodiments. All temperatures are in degrees Celsius.

EXAMPLE 1

1-(1-Oxo-2-propenyl)-L-proline

Method A

To a stirred solution of 5.76 g. (0.05 mol.) of L-proline and 4.94 g. (0.06 mol.) of sodium acetate in 100 ml. of acetic acid is added 5.54 g. (0.06 mol.) of acryloyl chloride. After one hour, the reaction mixture is concentrated to dryness and the remaining traces of acetic acid removed by adding 50 ml. of water and reconcentrating. The residue is then dissolved in 100 ml. of water and extracted with chloroform. Concentration of the dried (anhydrous magnesium sulfate), filtered extract gives an oily residue which is taken up in 5 ml. of acetonitrile and cooled to give 2.3 g. (27%) of colorless crystals, m.p. 118°–119° (dec.). Recrystallization from the same solvent gives 1.5 g. of 1-(1-oxo-2-propenyl)-L-proline, m.p. 118°–119°; $R_f$: 0.53 (silica gel-acetic acid, 5; dichloromethane, 90; methanol, 5).

Method B

To a stirred solution of 5.76 g. (0.05 mol.) of L-proline in 25 ml. of water maintained at 0° by an ice bath is added during 4 hours, a mixture of 4.5 g. (0.05 mol.) of acryloyl chloride and 5 ml. of methyl isobutyl ketone. Simultaneously with the addition of the acid chloride, 2 N sodium hydroxide is added maintaining the pH constant at 7.0+0.1.

After addition of the acid chloride is complete, the reaction mixture is stirred until the pH remains constant (about 1 hour) and the pH is then adjusted to 5.0. The mixture is extracted with 100 ml. of ethyl acetate, the pH then readjusted to 2.5, the mixture saturated with sodium chloride, and reextracted repeatedly with 100 ml. portions of the same solvent. The extracts are combined, dried (anhydrous magnesium sulfate) filtered, cooled, and 10.0 g. (0.055 mol.) of dicyclohexylamine is added. The colorless solid which separates is filtered and dried to give 4.9 g. (14%) of 1-(1-oxo-2-propenyl)-L-proline, dicyclohexylamine salt m.p., 174°–175° (dec.) acetonitrile).

The dicyclohexylamine salt is dissolved in 100 ml. of water, and the pH adjusted to 2.5 by dropwise addition of 20% hydrochloric acid. A voluminous precipitate of dicyclohexylamine hydrochloride separates and is filtered and washed well with ethyl acetate. The filtrate is then saturated with salt and extracted with the same solvent. Concentration of the combined, dried (anhydrous magnesium sulfate) extracts gives a viscous oil which is dissolved in a little acetonitrile and cooled to give 1.05 g. (12%) of colorless crystals identical with the product obtained according to Method A.

EXAMPLE 2

1-[1-Oxo-3-[(phenylmethyl)selenyl]propyl]-L-proline

To a mixture of 13.6 g. of dibenzyl diselenide in 80 ml. of ethanol and 40 ml. of benzene there is added in portions, a solution of 3.4 g. of sodium borohydride in 64 ml. of N sodium hydroxide. The initially yellow solution turns colorless. The solvents are evaporated and to the resulting residue there is added cautiously 2 N sulfuric acid until the pH reaches 1. The resulting benzyl selenol is extracted with ether. The dried extract (MgSO$_4$) is filtered and to the filtrate there is added 6.8 g. of 1-(1-oxo-2-propenyl)-L-proline and 50 ml. of ethanol. The ether is evaporated until a final volume of about 50 ml. is reached. The solution is kept 24 hours at room temperature after which the solvent is evaporated. On ether addition, solid 1-[1-oxo-3-[(phenylmethyl)selenyl]propyl]-L-proline forms, 12.8 g. which is crystallized from acetonitrile, m.p. 145°–146°.

EXAMPLE 3

1-(3-Bromo-1-oxopropyl)-L-proline

L-proline (5.75 g.) is dissolved in N sodium hydroxide with stirring in an ice bath. To this 50 ml. of N sodium hydroxide is added followed immediately by 3-bromopropanoyl chloride (8.5 g.). The pH is about 8 and the bath is removed. After 1.5 hours an additional 2.5 ml. of 2 N sodium hydroxide is added to bring the pH to 7. The reaction mixture is extracted twice with ether, the aqueous portion is acidified with concentrated hydrochloric acid and extracted into ethyl acetate. Yield 7.7 g. The 1-(3-bromo-1-oxopropyl)-L-proline is converted with dicyclohexylamine in ethyl acetate to the dicyclohexylamine salt, m.p. 284°–286°. This salt is then converted to the free acid with 10% potassium bisulfate in ethyl acetate. This product is recrystallized from ethyl acetate:hexane and recrystallized from ethyl acetate, m.p. 83°–85°.

EXAMPLE 4

1,1'-[Diselenobis(3-oxo-3,1-propanediyl)]bis-L-proline (a) A solution of 3 g. of sodium borohydride in 25 ml. of water is added in portions and with stirring (nitrogen atmosphere) to a suspension of 3 g. of selenium in 25 ml. of water. After the initial vigorous reaction has subsided, an additional 3 g. of selenium is added. The mixture is stirred for fifteen minutes and then warmed briefly on the steam bath to complete the reaction. The volume of the brownish-red solution of sodium diselenide is adjusted to 100 ml. with water and stored under nitrogen.

(b) To 30 ml. of the diselenide solution obtained in part (a) (nitrogen atmosphere) there is added at once a solution of 5.7 g. of 1-(3-bromo-1-oxopropyl)-L-proline which has been neutralized with potassium carbonate (about 20 ml. of final solution). The mixture becomes slightly exothermic. After one hour of stirring at room temperature, the yellow-brown solution is cooled and acidified with 10% potassium bisulfate. The product is extracted with 3×50 ml. of ethyl acetate. Evaporation of the dried extract (MgSO$_4$) yields 4 g. of yellow glassy oil. The oil is dissolved in chloroform and precipitated with ethyl ether. Cooling of this precipitate to 0° furnishes an amorphous, slightly yellow solid which turns oily at room temperature. The precipitation is repeated to yield, after drying in vacuo at 40°–45°, analytically pure product, 1,1'-[diselenobis(3-oxo-3,1-propanediyl)]bis-L-proline, as yellow foam.

Anal. Calc'd for $C_{16}H_{24}N_2O_6Se_2 \cdot H_2O$: C, 37.21; H, 5.07; N, 5.43 C, 37.45; H, 4.75; N, 5.35.

EXAMPLE 5

1-(3-Bromo-2-methyl-1-oxopropyl)-L-proline

To a solution of 6.75 g. of L-proline in 50 ml. of 1 N sodium hydroxide at 0° there are added 25 ml. of 2 N sodium hydroxide followed by 9.3 g. of 3-bromo-2-methylpropanoyl chloride and the mixture is stirred at 0° for three hours (monitored periodically to maintain basic pH). The mixture is extracted with ethyl ether. The aqueous portion is then acidified (HCl) and extracted with ethyl acetate. The ethyl acetate fractions are combined, dried ($MgSO_4$) and evaporated in vacuo to yield an oil which is triturated with petroleum ether (b.p. 30°–60°) and then with ethyl ether to give a white solid. Crystallization from ethyl ether yields 7.3 g. of 1-(3-bromo-2-methyl-1-oxopropyl)-L-proline m.p. 84°–86°.

EXAMPLE 6

1,1'-[Diselenobix(2-methyl-3-oxo-3,1-propanediyl)]-bis-L-proline (a) A solution of 4 g. of sodium borohydride in 25 ml. of water is added in portions and with stirring (under a nitrogen atmosphere) to a suspension of 4 g. of selenium in 25 ml. of water. After the initial vigorous reaction has subsided, an additional 4 g. of selenium is added. The mixture is stirred for 15 minutes and then warmed on the steam bath for about two minutes to complete the reaction. The volume of the brownish-red solution is adjusted to 100 ml. with water and stored under nitrogen.

(b) To 10 ml. of the diselenide solution from part a (under a nitrogen atmosphere) there is added all at once a solution of 2.6 g. of 1-(3-bromo-2-methyl-1-oxopropyl)-L-proline that has been neutralized with potassium carbonate (about 15 ml. of final solution) and the mixture is stirred at room temperature for three hours. The yellow-brown solution is acidified with 10% potassium bisultate and extracted with ethyl acetate. The organic layers are combined, dried ($MgSO_4$) and evaporated in vacuo to yield 1,1'-[diseleno-bis(2-methyl-3-oxo-3,1-propanediyl)]-bis-L-proline as a yellow glass (2.3 g.).

Anal. Calc'd for $C_{18}H_{28}N_2O_6Se_2$: C, 41.08; H, 5.37; N, 5.33: Found: C, 41.13; H, 5.62; N, 5.12.

EXAMPLE 7

1-[2-Methyl-1-oxo-3-[(phenylmethyl)selenyl]propyl]-L-proline

To a suspension of 1.7 g. of dibenzyldiselenide in 50 ml. of dry acetonitrile under nitrogen there is added 0.2 g. sodium borohydride and the mixture is heated until all yellow color disappears. The mixture is cooled, 2.6 g. of 1-(3-bromo-2-methyl-1-oxopropyl)-L-proline is added and the mixture is stirred at room temperature overnight. The solvent is removed in vacuo, water is added (pH=10) and the mixture is extracted with ethyl ether. The aqueous layer is then acidified (HCl) and extracted three times with ethyl acetate. The ethyl acetate fractions are combined, dried ($MgSO_4$), and evaporated to yield 2.1 g. of 1-[2-methyl-1-oxo-3-[(phenylmethyl)selenyl]propyl]-L-proline as a yellow oil.

Anal. Calc'd. for $C_{16}H_{21}NO_3Se$: C, 54.24; H, 5.97; N, 3.96: Found: C, 53.98; H, 6.00; N, 4.04.

EXAMPLE 8

1-[2-Methyl-1-oxo-3-(phenylselenyl)propyl]-L-proline

To a solution of 1.6 g. of diphenyl diselenide in 25 ml. of methanol (under nitrogen) is added sodium borohydride in portions until the solution is decolorized (yellow to colorless). To this solution is added 2.6 g. of 1-(3-bromo-2-methyl-1-oxopropyl)-L-proline and the mixture is stirred at room temperature for five hours. The solvent is removed in vacuo, water is added (pH=10) and the solution is extracted with ethyl ether. The aqueous portion is acidified (HCl) and extracted three times with ethyl acetate. The ethyl acetate layers are combined, dried ($MgSO_4$) and evaporated in vacuo to give 2.9 g. of 1-[2-methyl-1-oxo-3-(phenylselenyl)-propyl]-L-proline as a viscous yellow oil.

Anal. Calc'd. for $C_{15}H_{19}NO_3Se$. $\frac{3}{4}$ mole $H_2O$: C, 50.92; H, 5.84; N, 3.95: Found: C, 51.20; H, 5.74; N, 4.01.

EXAMPLE 9

1-[1-Oxo-4-[phenylmethyl)selenyl]butyl]-L-proline

Following the procedure of Example 7 and substituting 1-(4-bromo-1-oxobutyl)-L-proline for the 1-(3-bromo-2-methyl-1-oxopropyl)-L-proline, 1-[1-oxo-4-[(phenylmethyl)selenyl]butyl]-L-proline is obtained.

EXAMPLE 10

1,1'-[Diselenobis(4-oxo-4,1-butanediyl)]bis-L-pipecolic acid

Following the procedure of Example 4 and substituting 1-(4-bromo-1-oxobutyl)-L-pipecolic acid for 1-(3-bromo-1-oxopropyl)-L-proline, 1,1'-[diselenobis(4-oxo-4,1-butanediyl)]-bis-L-pipecolic acid is obtained.

EXAMPLE 11

1-(3-Selenyl-1-oxopropyl)-L-proline

To a solution of 1.5 g. of the product from Example 4 in 25 ml. of ethanol is added a solution of 0.23 g. of sodium borohydride in 10 ml. of 1 N sodium hydroxide and the stirred mixture is heated on the steam bath for about ten minutes. The solvent is evaporated, the residue is acidified with 2 N sulfuric acid and extracted with ethyl acetate. The dried extract is evaporated to yield 1-(3-selenyl-1-oxo-propyl)-L-proline.

EXAMPLE 12

1-[1-Oxo-3-[(benzoyl)selenyl]propyl]-L-proline

To a chilled solution of 0.5 g. of 1-(3-selenyl-1-oxopropyl)-L-proline dissolved in 5 ml. of pyridine there is added dropwise with stirring 0.3 g. of benzoyl chloride. The mixture is allowed to come to room temperature. After three hours, the solvent is evaporated. The residue is taken up in ethyl acetate, washed with saturated sodium bicarbonate solution and then with water. The solvent is dried, and evaporated to yield 1-[1-oxo-3-[(benzoyl)-selenyl]propyl]-L-proline.

EXAMPLES 13–26

Following the procedure of the indicated Example, and substituting the starting material having the substituents indicated below, the following compounds are obtained (the term "Bis" under $R_2$ indicates the symmetric diseleno dimer).

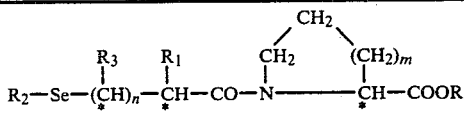

| Example | R | $R_1$ | $R_2$ | $R_3$ | m | n | Procedure of Example |
|---|---|---|---|---|---|---|---|
| 13 | H | H | $CH_3$ | H | 1 | 1 | 2 |
| 14 | H | H | $C_2H_5$ | H | 1 | 2 | 7 |
| 15 | $C_2H_5$ | $CH_3$ | Bis | H | 2 | 1 | 6 |
| 16 | H | $CH_3$ | H | $CH_3$ | 2 | 1 | 11 |
| 17 | $C_2H_5$ | $CH_3$ | $C_6H_5CH_2-$ | H | 2 | 1 | 7 |
| 18 | $C_6H_5$ | $CH_3$ | $C_6H_5CO-$ | H | 2 | 1 | 12 |
| 19 | H | H | $CH_3CO-$ | — | 1 | 0 | 11,12 |
| 20 | H | $C_2H_5$ | B is | — | 1 | 0 | 6 |
| 21 | $C_6H_5CH_2-$ | $CH_3$ | $C_6H_5$ | $CH_3$ | 1 | 1 | 7 |
| 22 | H | H | H | — | 1 | 0 | 11 |
| 23 | H | $CH_3$ | $C_3H_7$ | H | 2 | 1 | 7 |
| 24 | H | $CH_3$ | $C_6H_5$ | $C_2H_5$ | 1 | 1 | 7 |
| 25 | H | H | $C_6H_5CH_2-$ | — | 2 | 0 | 7 |
| 26 | H | $CH_3$ | H | H | 1 | 1 | 11 |

What is claimed is:

1. A compound of the formula

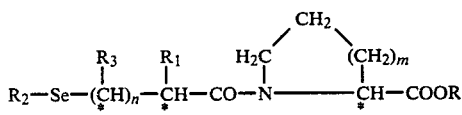

wherein
R is hydrogen, lower alkyl, phenyl or phenyl-lower alkyl;
$R_1$ and $R_3$ each is hydrogen or lower alkyl;
$R_2$ is hydrogen, lower alkyl, lower alkanoyl, benzoyl, phenyl-lower alkyl, phenyl or

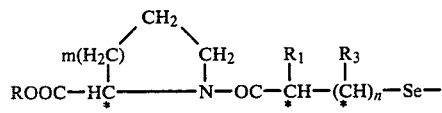

m is 1 or 2; and
n is 0, 1 or 2.

2. A compound as in claim 1 wherein R and $R_1$ each is hydrogen or lower alkyl; $R_2$ is hydrogen, lower alkanoyl, phenylmethyl, phenyl or

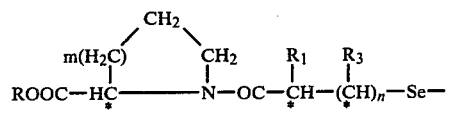

$R_3$ is hydrogen; m and n each is 1 or 2.

3. A compound as in claim 1 wherein m is 1.

4. A compound as in claim 1 wherein m is 2.

5. A compound as in claim 1 wherein R is hydrogen.

6. A compound as in claim 1 wherein $R_2$ is hydrogen.

7. A compound as in claim 1 wherein $R_2$ is

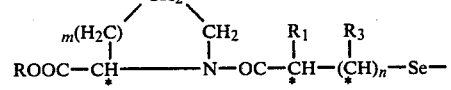

8. A compound as in claim 1 wherein R, $R_1$ and $R_3$ each is hydrogen; $R_2$ is phenylmethyl; and m and n each is 1.

9. The L-form of the compound of claim 8 having the name 1-[1-oxo-3-[(phenylmethyl)selenyl]propyl]-L-proline.

10. A compound as in claim 7 wherein each R, $R_1$ and $R_3$ is hydrogen; and each m and n is 1.

11. The L-form of the compound of claim 10 having the name 1,1'-[diselenobis(3-oxo-3,1-propanediyl)]bis-L-proline.

12. A compound as in claim 7 wherein each R and $R_3$ is hydrogen; each $R_1$ is methyl; and each m and n is 1.

13. A compound as in claim 1 wherein R, $R_2$ and $R_3$ each is hydrogen; $R_1$ is methyl; and m and n each is 1.

* * * * *